United States Patent [19]
Takahashi et al.

[11] Patent Number: 4,709,082
[45] Date of Patent: Nov. 24, 1987

[54] 2-PHENYLPROPIONIC ACID ESTERS, METHOD FOR OPTICAL RESOLUTION THEREOF AND OPTICALLY ACTIVE SUBSTANCE THEREOF

[75] Inventors: Yasuhiro Takahashi, Chiba; Kazutaka Arai, Yotsukaido; Yoshio Ohara, Narashino; Hiroo Matsumoto, Funabashi; Syuuzi Tsuchiya, Shiroimachi, all of Japan

[73] Assignee: Nissan Chemical Industries, Ltd., Tokyo, Japan

[21] Appl. No.: 789,640

[22] Filed: Oct. 21, 1985

[30] Foreign Application Priority Data

Oct. 25, 1984 [JP] Japan ................................ 59-224742
Oct. 25, 1984 [JP] Japan ................................ 59-224743

[51] Int. Cl.$^4$ ............................................. C07C 69/76
[52] U.S. Cl. .................................................... 560/105
[58] Field of Search ........................................ 560/105

[56] References Cited

U.S. PATENT DOCUMENTS 3,641,161  2/1972  Fried et al. .......................... 560/105
4,299,844  11/1981  Goudie ................................ 560/105

FOREIGN PATENT DOCUMENTS 0048433  3/1982  European Pat. Off. ............ 560/105
3116474  11/1982  Fed. Rep. of Germany .

OTHER PUBLICATIONS

Brown, J. M., J.C.S. Chem. Comm. 1974, pp. 969–971.
Chemical Abstracts, 89, 1978, p. 726, 89: 107233q.
Chemical Abstracts Service Registry Handbook, 1975 Supplement 55019-71-1 & 55019-72-2.
Chem. Abstracts, 86, 1977, p. 475, 86:170527v.

Primary Examiner—Paul J. Killos
Attorney, Agent, or Firm—Frishauf, Holtz, Goodman & Woodward

[57] ABSTRACT

2-Phenylpropoionic acid ester of Formula (I):

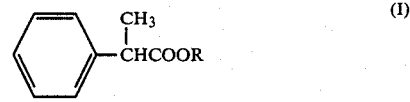

wherein R represents p-nitrophenyl group, β-naphthyl group or 2-(β-naphthyl)ethyl group.

Optical resolution of the above is carried out by preferential crystallization by seeding either one of the optical isomers into a super-saturated solution of a racemic modification thereof or a mixture of the optical isomers thereof. The efficiency of the optical resolution can be increased by optional addition of a recemizing agent comprising a strongly basic amine or an alcholate.

20 Claims, No Drawings

2-PHENYLPROPIONIC ACID ESTERS, METHOD FOR OPTICAL RESOLUTION THEREOF AND OPTICALLY ACTIVE SUBSTANCE THEREOF

BACKGROUND OF THE INVENTION

This invention relates to 2-phenylpropionic acid esters represented by Formula (I):

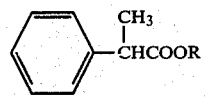
(I)

wherein R represents p-nitrophenyl group, β-naphthyl group or 2-(β-naphthyl)ethyl group,
and a method for optical resolution of the optical isomers thereof, and also an optically active substance thereof.

By hydrolyzing the optical isomers of these esters in the retention of the configurations, optically active 2-phenylpropionic acids can readily be obtained.

Optically active 2-phenylpropionic acid is a useful compound to be used widely as a resolving agent for bases, and it is also useful as an intermediate compound or modifying agent of pharmaceuticals, agricultural chemicals, etc.

In the prior art, as the method for preparation of optically active 2-phenylpropionic acid capable of optical resolution of a racemic modification, the following methods have been known:

(a) Diastereomer resolution method by salt formation with a basic resolving agent: for example, the method in which α-phenethylamine is used as the resolving agent [see Arkivkemi., 10, 283 (1956)], similarly the method in which α-phenyl-β-(p-tolyl)ethylamine is used [see Japanese Unexamined Patent Publication No. 63946/1981];

(b) Diastereomer resolution method by ester formation with an optically active alcohol: for example, the method in which (—)-menthyl ester is obtained as an intermediate [see German OLS DE.3116474], the method in which α-phenethyl ester is obtained as an intermediate [see Angew. Chem. 93, 919 (1981)].

On the other hand, concerning the compounds of the present invention, both optical isomers and racemic modification have not been known in the art for β-naphthyl ester and 2-(β-naphthyl)ethyl ester of 2-phenylpropionic acid. Also, as for p-nitrophenyl ester of 2-phenylpropionic acid, although there are descriptions thereabout in Chemical Abstracts 89, 107223q (original report, Ciba Found. Symp., 53, 149 (1978)) and 84, 16437t (original report, J.C.S. Chem. Commun., 969 (1974)), there is no description about the physical properties and the method for preparation in any of these literatures. Thus, it may be said that these compounds has been isolated and purified for the first time in the present invention.

Any of the techniques for preparation of optically active 2-phenylpropionic acid by optical resolution of the prior art requires an expensive resolving agent. Also, when the useless optical isomer of 2-phenylpropionic acid is racemized for reuse, the method of (a) is unpractically too slow in racemization. On the other hand, according to the method of (b), in addition to the problem of no realization of complete racemization due to influence by the optically active alcoholic moiety, there is also involved the problem of side reaction which causes the optical purity of the alcoholic moiety to be lowered. Thus, both the methods (a) and (b) can hardly be said to be practical preparation methods.

To the contrary, the method by way of preferential crystallization requires no expensive resolving agent, and it is an advantageous method which enables optical resolution by crystallization operation employing a small amount of seed crystals. However, so far as 2-phenylpropionic acid is concerned, no compound for which this method is applicable has been known at all.

SUMMARY OF THE INVENTION

The present inventors have searched for various ester derivatives which can also be racemized easily, in order to apply the preferential crystallization method for optical resolution of 2-phenylpropionic acid, and consequently found that 2-phenylpropionic acid esters represented by the formula (I) are compounds which have an ability for preferential crystallization.

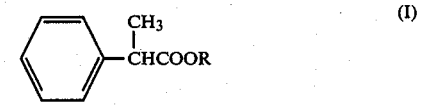
(I)

wherein R represents p-nitrophenyl group, β-naphthyl group or 2-(β-naphthyl)ethyl group, Optical resolution of the 2-phenylpropoionic acid ester of Formula (I) is carried out by a method which comprises (i) effecting crystallization for optical resolution by seeding either one of the optical isomers of said 2-phenylpropionic acid ester into a super-saturated solution of a racemic modification of said ester or a mixture in which one of the optical isomers of said ester exists in excess over the other optical isomer; said solution optionally containing a racemizing agent comprising a strongly basic amine or ROM wherein R represents the R of the 2-phenylpropionic acid ester dissolved, and M represents sodium, potassium, lithium or calcium (½ Ca); or (ii) subjecting a super-saturated solution of a racemic modification of said ester or a mixture in which one of the optical isomers of said ester exists in excess over the other optical isomer to spontaneous crystallization. The (±)-2-phenylpropionic acid esters of the present invention can be synthesized according to the known ester synthetic method such as the reaction between (±)-2-phenylpropionic acid or its acid chloride and p-nitrophenol, β-naphthol or 2-(8-naphtyl)ethyl alcohol, respectively.

Also, the optically active 2-phenylpropionic acid esters of the present invention can be synthesized by esterification of the optically active 2-phenylpropionic acids, respectively, or alternatively by optical resolution of the (±)-2-phenylpropionic acid ester as shown below.

For resolution of these according to the preferential crystallization method of the present invention, it can be accomplished by adding seed crystals of (+)—isomer or (—)—isomer to a super-saturated solution of racemic modification, and crystallizing preferentially the optical isomer of the same kind as the isomer added. Also, a super-saturated solution of a mixture resolved partially (namely, one of the optical isomers occurs more abundantly) can similarly be used and, in this case, no seed crystal is required to be added externally but resolution will proceed through spontaneous crystallization.

These super-saturated solutions can be prepared according to conventional methods such as the method in which racemic modification or a mixture partially resolved is dissolved by heating in an appropriate solvent, followed by cooling; the method in which the solution is concentrated; the method in which a solvent as will reduce the solubility is added; etc.

As the solvent to be used for resolution, it is preferable to use a solvent in which the 2-phenylpropionic acid ester exhibits suitable solubility, preferably a solvent in which the solubility of the racemic modification of the 2-phenylpropionic acid ester is higher than that of the optical isomers of said ester. For example, there may be employed petroleum ether, benzine, ligroin, aliphatic hydrocarbons such as n-hexane or cyclohexane, aromatic hydrocarbons such as benzene or toluene, ethers such as ethyl ether or isopropyl ether, halogenated hydrocarbons such as carbon tetrachloride, chloroform or dichloromethane, esters such as ethyl acetate, alcohols such as methanol, ethanol, isopropanol, n-propanol or t-butanol, aprotic polar solvents such as acetone, methyl ethyl ketone, dimethyl formamide (DMF) or dimethyl sulfoxide (DMSO), and mixtures thereof. When a base is permitted to coexist for racemization, a solvent which can react with such a base should be avoided.

The amount and the particle size of the seed crystals added are not particularly limited, but it is generally suitable to use the crushed powder of seed crystals of about 1 to 20% by weight based on the racemic modification or the partially resolved mixture in the solution.

The operational temperature is not also particularly limited, and a temperature up to the boiling point of the solvent can be applied. However, it is necessary to control the temperature so that a stable super-saturated solution may be obtained, depending on the solubility of the 2-phenylpropionic acid ester relative to the solvent to be employed.

As the method for resolution, there may be employed various methods known as a preferential crystallization method in the art, including the batch method in which the opposite optical active isomers are alternately resolved, the continuous method in which seed crystals are permitted to exist in a column and the super-saturated solution is permitted to flow through the column, and the method in which one optically active isomer and the other optically active isomer are immersed as seed grains in places with certain intervals therebetween and the respective seed grains are allowed to grow at the same time, etc.

The optically active 2-phenylpropionic acid ester thus obtained, if it is insufficient in optical purity, can further be enhanced in optical purity by recrystallization, etc.

In the case of permitting a racemizing agent to coexist, it is possible to use as the racemizing agent (i) an alkali metal salt or an alkaline earth metal salt (e.g. sodium salt, potassium salt, lithium salt or calcium salt) of p-nitrophenol, β-naphthol or 2-(β-naphthyl)ethanol corresponding respectively to the ester portion of the ester employed or (ii) a nitrogen-containing base including triethylamine, 1,8-diazabicyclo[5.4.0]undec7-ene (DBU), 1,5-diazabicyclo[4.3.0]-non-5-ene (DBN) or 1,4-diazabicyclo[2.2.2]octane (DBO).

Also, the concentration of the racemizing agent may preferably be as much as possible for acceleration of the racemization reaction. However, if it is too much, the viscosity of the solution may become too high, or side reactions may occur. Although it may differ depending on the strength of the base, for example, in the case of a strong base such as diazabicycloundecene (DBU) or diazabicyclononene (DBN), the concentration should preferably be about 0.1 to 20% (w/w).

The present invention is described in more detail by referring to the following Examples. However, the present invention is not limited by these Examples.

EXAMPLE 1

Synthesis of (±)-p-nitrophenyl ester:

(±)-2-Phenylpropionic acid in the amount of 7.50 g (50 mmol) and 7.14 g (60 mmol) of thionyl chloride were heated for 1 hour under reflux in carbon tetrachloride. The solvent and unaltered thionyl chloride were evaporated under reduced pressure to give (±)-2-phenylpropionic acid chloride as a pale yellow oil. To the oil were added 30 ml of benzene, 7.30 g (52.5 mmol) of p-nitrophenol and 4.75 g (60.0 mmol) of pyridine were added, and the mixture was stirred at room temperature for 2 hours. The reaction mixture was diluted with 10 ml of aqueous 10% hydrochloric acid, extracted with ethyl acetate, followed by solvent evaporation from the organic layer, to obtain 13.9 g of a pale yellow solid. Recrystallization of the solid from ethanol gave 10.4 g (38.4 mmol, yield 77%) of (±)-p-nitrophenyl 2-phenylpropionate as colorless crystals.

m.p. 55.0–56.5° C.;

$_1$H NMR: (CDCl$_3$) δ:1.60(d, 3H, J=6Hz), 3.97 (q, 1H, J=6Hz), 7.0–8.2(m, 9H);

IR (KBr): 1745, 1530, 1340, 1200, 1140, 1080, 900, 870, 740, 700 cm$^{-1}$.

MS, m/e (intensity ratio): 271 (M+, 4), 133 (34), 105 (100);

$[\alpha]_D^{25} 0°$.

EXAMPLES 2 to 6

Syntheses of various esters of 2-phenyl-propionic acid:

The reactions between (+), (−) or (±) isomer of 2-phenylproionic acid with p-nitrophenol, β-naphthol or 2-(β-naphthyl)ethanol, and the post-treatments were conducted following the procedure of Example 1. (When the mole scale of the reaction was changed, the amounts of the solvent, the starting materials employed were changed at the same ratio as the change ratio of mole scale.) The results of these reactions are shown below.

EXAMPLE 2

Synthesis of (−)-p-nitrophenyl ester:

Reaction mole scale: 7.0 mmol (moles of the starting 2-phenylpropionic acid);

Kind of 2-phenylpropionic acid: (−)-isomer, $[\alpha]_D^{25}$ −79.1°(c=1, EtOH) (100% e.e.);

Kind of phenol or alcohol: p-nitrophenol

Yield: 83% m.p.: 78.5–79.0° C. (recrystallized from ethanol);

MS, m/e (intensity ratio), $^1$H NMR: (CDCl$_3$) δ and IR (KBr): the same as in Example 1;

$[\alpha]_D^{25}$ −134.5° (c=1, EtOH) (100% e.e.).

EXAMPLE 3

Synthesis of (±)-β-naphthyl ester:

Reaction mole scale: 10.0 mmol (moles of the starting 2-phenylpropionic acid);

Kind of 2-phenylpropionic acid: (±)-isomer;

Kind of phenol or alcohol: β-naphthol;
Yield: 67%;
m.p.: 54°–55.0° C. (recrystallized from isopropanol);
MS, m/e (intensity ratio): 276 (M+, 23), 144(96), 132(100), 105(84);
$^1$H NMR: (CDCl$_3$): 1.52(d, 3H, J=6Hz), 4.00 (q, 1H, J=6Hz), 7.0–7.9 (m, 12H);
IR (KBr): 1740, 1450, 1140, 1060, 910, 820, 750, 700 cm$^{-1}$;
$[\alpha]_D^{25}$ 0°.

EXAMPLE 4

Synthesis of (+)-β-naphthyl ester:

Reaction mole scale: 4.0 mmol (moles of the starting 2-phenylpropionic acid);
Kind of 2-phenylpropionic acid: (+)-isomer, $[\beta]_D^{25}$ +79.1°(c=1, EtOH) (100% e.e.);
Kind of phenol or alcohol: β-naphthol;
Yield: 52%;
m.p.: 78.0°–78.5° C. (recrystallized from isopropanol);
MS, m/e (intensity ratio), $^1$H NMR: (CDCl$_3$) δ and IR (KBr): the same as in Example 3;
$[\alpha]_D^{25}$ −134.5° (c=1, EtOH) (100% e.e.).

EXAMPLE 5

Synthesis of (±)-2-(β-naphthyl)ethyl ester:

Reaction mole scale: 10.0 mmol (moles of the starting 2-phenylpropionic acid);
Kind of 2-phenylpropionic acid: (±)-isomer;
Kind of phenol or alcohol: 2-(β-naphthyl)ethanol
Yield: 79%
m.p.: 68.0°–69.0° C. (recrystallized from ethanol);
MS, m/e (intensity ratio): 304(M$^\pm$, 6), 154 (100);
$^1$H NMR: (CDCl$_3$) δ: 1.48(d, 3H, J=6Hz), 3.00 (t, 2H, J=6Hz), 3.66 (q, 1H, J=6Hz), 4.35 (t, 2H, J=6Hz), 7.1 7.9 (m, 12H);
IR (KBr): 1720, 1330, 1200, 1165, 1100, 960, 825, 750, 705 cm$^{-1}$; $[\alpha]_D^{25}$ 0°.

EXAMPLE 6

Synthesis of (+)-2-(β-naphthyl)ethyl ester:

Reaction mole scale: 1.8 mmol (moles of the starting 2-phenylpropionic acid);
Kind of 2-phenylpropionic acid: (+)-isomer, $[\alpha]_D^{25}$ +79.1°(c=1, EtOH) (100% e.e.);
Kind of phenol or alcohol: 2-(β-naphthyl)ethanol;
Yield: 59%;
m.p.: 89.5°–90.5° C. (recrystallized from ethanol);
MS, m/e (intensity ratio), $^1$H NMR: (CDCl$_3$) and IR (KBr): the same as in Example 5;
$[\alpha]_D^{25}$ +22.5° (c=0.5, EtOH) (100% e.e.).

EXAMPLE A-1

Preferential crystallization by addition of seed crystals of p-nitrophenyl ester (±)-p-Nitrophenyl 2-phenylpropionate (0.505 g) was dissolved by heating in 9.780 g of ethanol. The solution was cooled to 20° C., and 100 mg of powdered crystals of (−)-p-nitrophenyl 2-phenylpropionate were seeded thereto. The mixture was stirred at 20° C. for 30 minutes, then under cooling at a cooling rate of 1° C./hr to 16° C., and thereafter the crystals were separated by filtration and dried. Yield of crystals: 130 mg. $[\alpha]_D^{25}$ −131.8° (c=1.0, EtOH), 98.0% e.e.

The optical rotation of p-nitrophnyl 2-phenylpropionate on the filtrate side was found to be $[\alpha]_D^{25}$ +11.2° (c=1.0, EtOH), 8.3% e.e.

EXAMPLE A-2

Preferential crystallization by addition of seed crystals of 2-(β-naphthyl)ethyl ester (±)-2-(β-Naphthyl)ethyl 2-phenylpropionate (1.00 g) was dissolved by heating in 24.66 g of ethanol. The solution was cooled to 29° C., and 51 mg of powdery crystals of (±)-2-(β-naphthyl)ethyl 2-phenylpropionate ($[\alpha]_D^{25}$ +22.5° (c=0.5, EtOH), 100% e.e. were added. The mixture was stirred at 29° C. for 30 minutes, then under cooling at a cooling rate of 1° C./hr to 23° C., and thereafter the crystals were separated by filtration and dried. Yield of crystals: 120 mg. $[\alpha]_D^{25}$ +20.8° (c=0.5, EtOH), 92.4% e.e.

The optical rotation of 2-(β-naphthyl)ethyl 2-phenylpropionate on the filtrate side was found to be $[\alpha]_D^{25}$ −0.8° (c=0.5, EtOH), 3.6% e.e.

EXAMPLE A-3

Preferantial crystallization of β-naphthyl eester under co-presence of a racemizing agent:

(±)-β-Naphthyl 2-phenylpropionate (2.00 g) was dissolved in 1.84 g of a 5 wt. % solution of diazabicycloundecene (DBU) in cumene at 30° C., and then 100 mg of (±)-β-naphthyl 2-phenylpropionate ($[\alpha]_D^{25}$ +130° (c=1.0, EtOH), 96% e.e.) was added to the solution at 24° C. After the mixture was stirred at 24° C. for 30 minutes, it was cooled to 14° C. at a cooling rate of 0.5° C./hr, followed further by stirring at 14° C. for 2 hours. The crystals were collected by filtration, washed with cold ethanol and dried to give 706 mg of colorless crystals. $[\alpha]_D^{25}$ +130° (c=1.0, EtOH), 96% e.e. As a consequence, 682 mg of (+)-isomer was obtained, which corresponded to 29% of the starting material, excluding the seed crystals.

EXAMPLE A-4

Preferential crystallization of β-naphthyl ester under co-presence of a racemizing agent: (±)-β-Naphthyl 2-phenylpropionate (2.625 g) was dissolved in 3.09 g of a 5 wt. % solution of diazabicycloundecene (DBU) in isopropyl ether at 35° C., and then 100 mg of (+)-β-naphthyl 2-phenylpropionate ($[\alpha]_D^{25}$ +135.3° (c=1.0, EtOH), 100% e.e.) was added to the solution at 29° C. After the mixture was stirred at 28° C. for 30 minutes, it was cooled to 10° C. at a cooling rate of 1.0° C./hr, followed further by stirring at 10° C. for 2 hours. The crystals were collected by filtration, washed with cold ethanol and dried to give 1.847 g of colorless crystals. $[\alpha]_D^{25}$ +132.4° (c=1.0, EtOH), 97.9% e.e.

As a consequence, 1.807 of (+)-isomer was obtained, which corresponded to 64% of the (±)-isomer of the starting material, excluding the seed crystals.

REFERENCE EXAMPLE 1

Preparation of optically active 2-phenylpropionic acid by hydrolysis of optically active β-naphthyl 2-phenylpropionate To 1.00 g of (+)-β-naphthyl 2-phenylpropionate (3.62 mmol, $[\alpha]_D^{25}$ +135.3° (c=1.0, EtOH), 100% e.e.) were added 1.00 g of 35% hydrochloric acid and 3.00 g of acetic acid, and the mixture was stirred under heating at 120° C. for 20 minutes. The reaction mixture was cooled, and 15 ml of toluene and 5 ml of water were added thereto, followed by separation into liquids. The toluene layer was washed with water (2×5 ml) and mixed thoroughly under shaking with addition of 40 g of 0.1 N aqueous sodium hydroxide, followed by separation into liquids.

The solvent was evaporated from the toluene layer, and the residue was dried to give 0.51 g (3.54 mmol, 98% recovery) of β-naphthol as pale brown crystals.

On the other hand, the alkaline layer was made acidic with addition of 0.50 g of 35% hydrochloric acid, extracted with 15 ml of toluene. The solvent was evaporated from the toluene layer and the residue dried to obtain 0.49 g of (+)-2-phenylpropionic acid (3.27 mmol, 90% recovery) as a colorless oil. $[\alpha]_D^{25} +75.7°$ (c=1.0, EtOH), 96% e.e.

We claim:

1. A method for optical resolution of a 2-phenylpropionic acid ester of Formula (I):

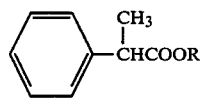

wherein R represents p-nitrophenyl group, 8-naphthyl group or 2-(β-naphthyl)ethyl group,
which comprises
(i) effecting crystallization for optical resolution by seeding either one of the optical isomers of said 2-phenylpropionic acid ester into a super-saturated solution of a racemic modification of said ester or a mixture in which one of the optical isomers of said ester exists in excess over the other optical isomer; said solution optionally containing a racemizing agent comprising a strongly basic amine or ROM wherein R represents the R of the 2-phenylpropionic acid ester dissolved, and M represents sodium, potassium, lithium or calcium (½ Ca); or
(ii) subjecting a super-saturated solution of a racemic modification of said ester or a mixture in which one of the optical isomers of said ester exists in excess over the other optical isomer to spontaneous crystallization.

2. The method according to claim 1, wherein the optical resolution is carried out by effecting crystallization resolution by seeding either one of the optically active isomers of said 2-phenylpropionic acid ester into a super-saturated solution of a racemic modification of said ester or a mixture in which one of the optical isomers of said ester exists in excess over the other optical isomer.

3. The method according to claim 1, wherein the optical resolution is carried out by effecting crystallization resolution by seeding either one of the optically active isomers of said 2-phenylpropionic acid ester into a super-saturated solution of a racemic modification of said ester or a mixture in which one of the optical isomers of said ester exists in excess over the other optical isomer; said solution containing a racemizing agent comprising a strongly basic amine or ROM wherein R represents the R of the 2-phenylpropionic acid ester dissolved, and M represents sodium, potassium, lithium or calcium (½ Ca).

4. The method according to claim 1, wherein the optical resolution is carried out by subjecting a super-saturated solution of a racemic modification of said ester or a mixture in which one of the optical isomers of said ester exists in excess over the other optical isomer, to spontaneous crystallization.

5. 1 The method according to claim 1, wherein said super-saturated solution comprises a solvent which is capable of dissolving the racemic modification of said 2-phenylpropionic acid ester represented by Formula (I) in an amount more than the optical isomers of said ester.

6. The method according to claim 5, wherein the solvent in the super-saturated solution is ethanol, isopropyl ether, cumene or a toluene-heptane solvent mixture.

7. The method according to claim 3, wherein said strongly basic amine for the racemizing agent is 1,8-diazabicyclo[5.4.0]undec-7-ene, 1,5-diazabicyclo[4.3.0]non-5-ene or 1,4-diazabicyclo[2.2.2]octane.

8. The method according to claim 7, wherein the strongly basic amine is 1,4-diazabicyclo[2.2.2]octane.

9. A 2-phenylpropoionic acid ester of the formula

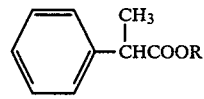

wherein R represents β-naphthyl group or 2-(β-naphthyl)ethyl group.

10. An optically active substance of a 2-phenylpropionic acid ester of the formula:

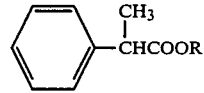

wherein R represents, β-naphthyl group or 2-(β-naphthyl)ethyl group.

11. The compound of claim 9 which is β-naphthyl 2-phenylpropionate.

12. The compound of claim 9 which is 2-(β-naphthyl)ethyl 2-phenylpropionate.

13. The optically active substance of claim 10 which is optically active β-naphthyl 2-phenylpropionate.

14. The optically active substance of claim 10 which is optically active 2-(β-naphthyl)ethyl 2-phenylpropionate.

15. The method according to claim 1, wherein said 2-phenylpropionic acid ester is p-nitrophenyl 2-phenylpropionate.

16. The method according to claim 1, wherein said 2-phenylpropionic acid ester is β-naphthyl 2-phenylpropionate.

17. The method according to claim 1, wherein said 2-phenylpropionic acid ester is 2-(β-naphthyl)ethyl 2-phenylpropionate.

18. The method according to claim 2, wherein said 2-phenylpropionic acid ester is p-nitrophenyl 2-phenylpropionate.

19. The method according to claim 2, wherein said 2-phenylpropionic acid ester is β-naphthyl 2-phenylpropionate.

20. The method according to claim 2, wherein said 2-phenylpropionic acid ester is 2-(β-naphthyl)ethyl 2-phenylpropionate.

* * * * *